United States Patent
Akerfeldt et al.

[11] Patent Number: 6,090,052
[45] Date of Patent: Jul. 18, 2000

[54] GUIDE WIRE HAVING A MALE CONNECTOR

[75] Inventors: Dan Akerfeldt; Per Egneloev, both of Uppsala, Sweden

[73] Assignee: Radi Medical Systems AB, Uppsala, Sweden

[21] Appl. No.: 09/047,456

[22] Filed: Mar. 25, 1998

Related U.S. Application Data

[60] Provisional application No. 60/042,396, Mar. 25, 1997.

[51] Int. Cl.[7] .......................................... A61B 5/00
[52] U.S. Cl. .............................. 600/585; 604/95; 604/280
[58] Field of Search .................................... 600/585, 433, 600/434, 437, 459, 462, 466; 604/95, 96, 280, 281

[56] References Cited

U.S. PATENT DOCUMENTS 5,178,159  1/1993  Christian ................................ 128/772
5,445,155  8/1995  Sieben ................................... 600/437

*Primary Examiner*—Pamela Wingood
*Attorney, Agent, or Firm*—Foley & Lardner

[57] ABSTRACT

The present invention relates to a guide wire, comprising a core wire (4) having a proximal and a distal end. There is at least one electrical lead (10a, 10b, 10c) provided on said core wire and extending along the length thereof, connecting to an electrical device (6) provided at the distal end of said core wire. A male connector is provided at the proximal end of said core wire, and a protective tubing (not shown) covers the core wire and the leads. The leads are formed on a sheet (14) of a thin, flexible material, said sheet being at least partially wrapped around said core wire along the length thereof. The flexible sheet has a wider portion (18) at the proximal end, and is wrapped at least one full turn around the proximal end of said core wire. The wider portion has at least one conductive strip (8a, 8b, 8c) extending over said portion in the transverse direction.

17 Claims, 5 Drawing Sheets

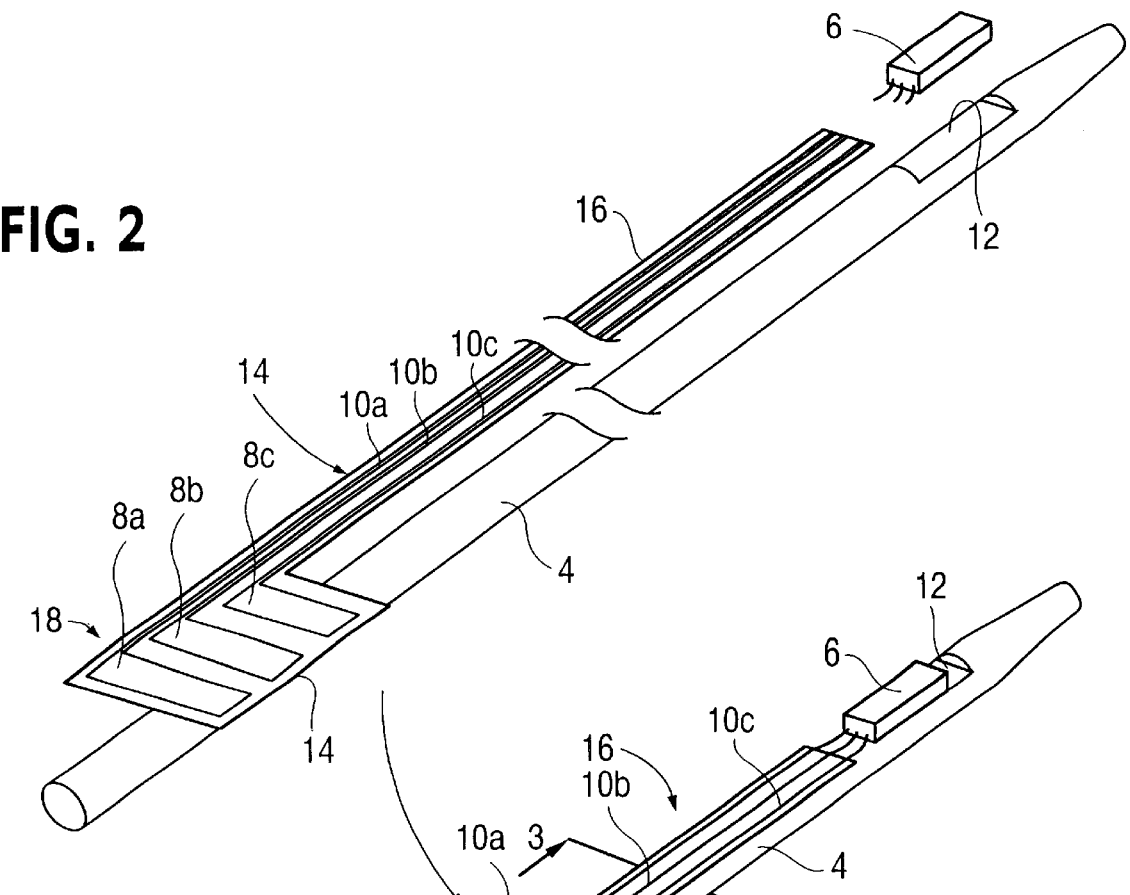
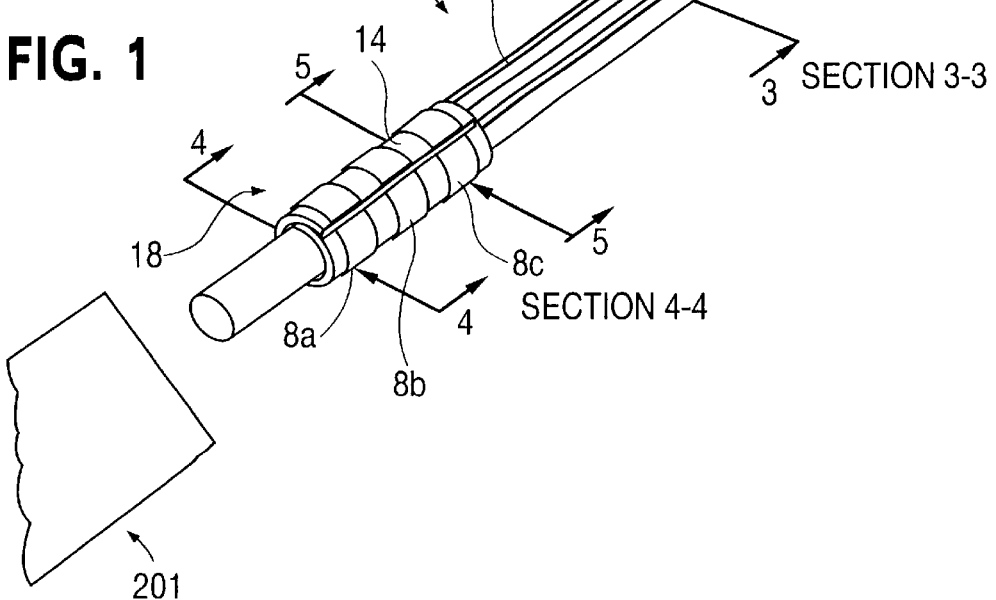
FIG. 2
FIG. 1

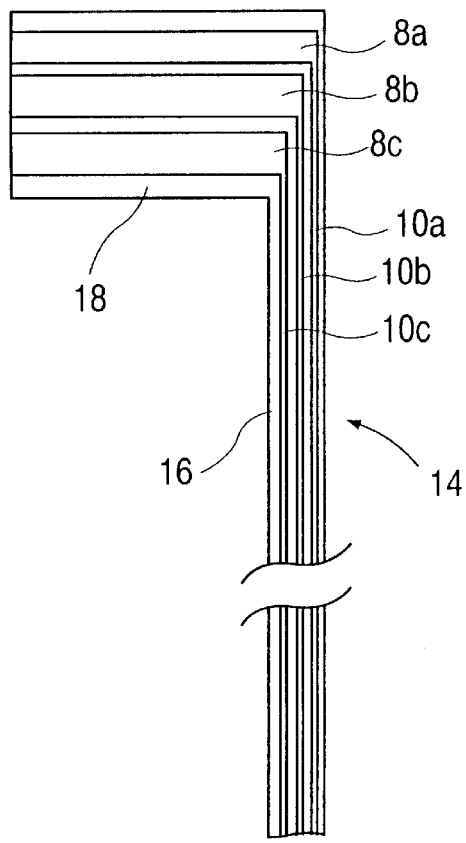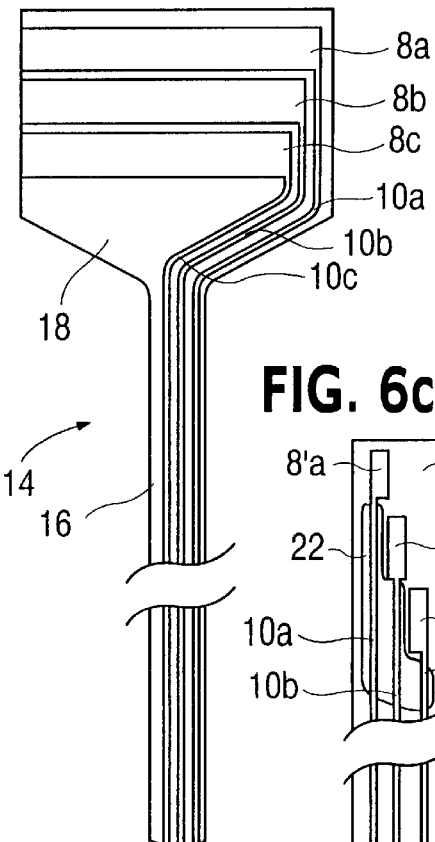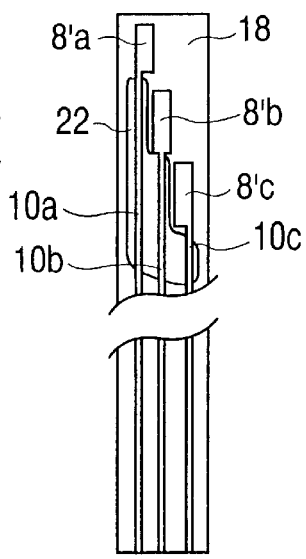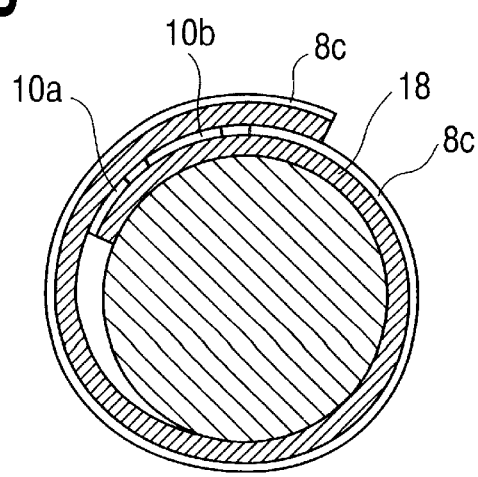

COPPER ETCHED AWAY TO CREATE THE CIRCUIT PATTERN.

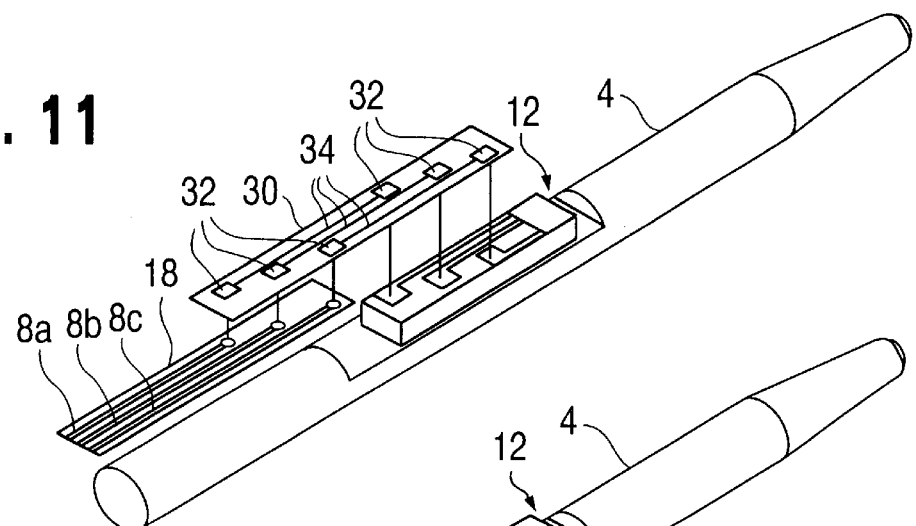
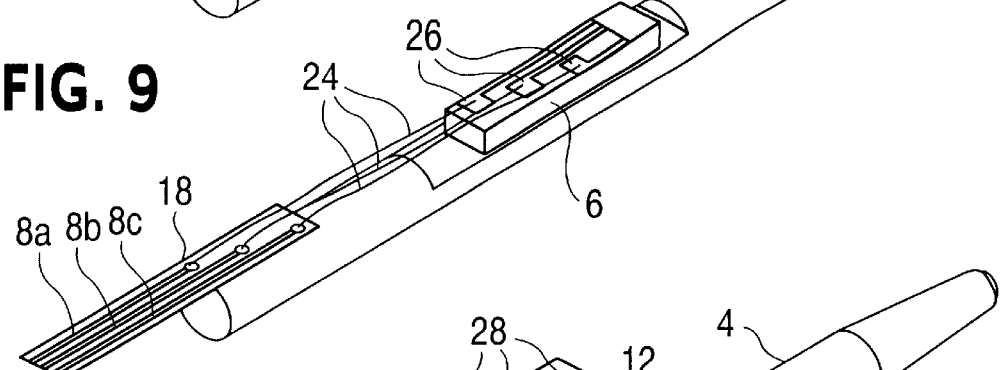
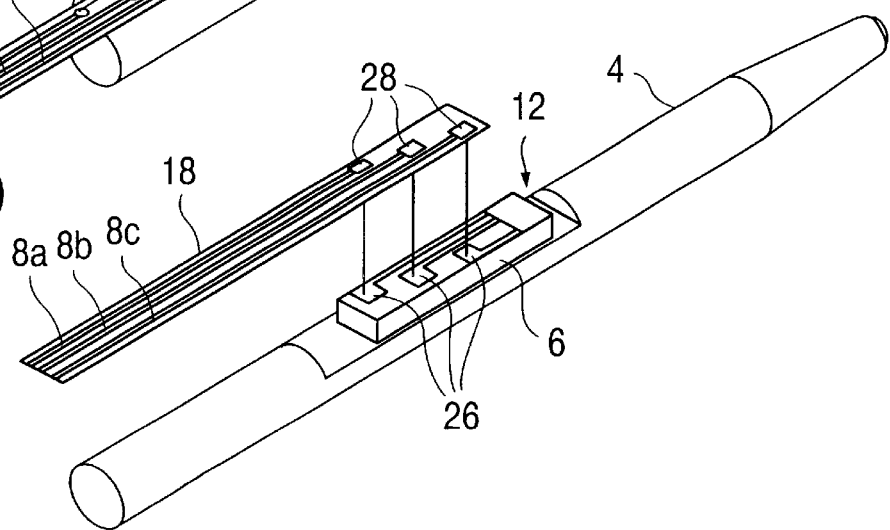

GUIDE WIRE HAVING A MALE CONNECTOR

The Applicants hereby claim the benefit of provisional application No. 60/042,396, filed Mar. 25, 1997.

the present invention relates to guide wires having a sensor at the distal end electrical leads running inside said guide wire and a male connector at the proximal end. The male connector interconnects the guide wire and an interface cable, connectable to external electronic devices, and having a mating female contact.

BACKGROUND OF THE INVENTION

A connector for guide wires of the kind mentioned above is disclosed in U.S. Pat. No. 5,178,159 (corresponding to EP-0 466 424). This disclosure teaches a design of the connector comprising providing each lead with a separate contact ring, mounted sequentially and isolated from each other on the guide wire at the proximal end. A disadvantage with this design is that traditional leads having circular cross section, and having a sufficiently large diameter, are difficult to accommodate in the space between the core wire and the protective tubing enclosing the core wire. Furthermore, it is difficult to solder the contact ring and the electrical lead without damaging or short circuiting the other leads passing underneath the contact ring in question.

SUMMARY OF THE INVENTION

The object of the present invention is thus to provided a connector of the type discussed above, which is easy to manufacture and which eliminates the risks for short-circuiting. This object is achieved by the invention, whereby the above disadvantages in connection with prior art connectors are overcome.

Thus, according to the invention there is provided a guide wire, comprising a core wire having a proximal and a distal end, electrical leads provided on said core wire and extending along the length thereof, and connecting to an electrical device provided at the distal end of said core wire, a male connector provided at the proximal end of said core wire, and a protective layer covering the core wire and the leads, said leads being formed on a sheet of a thin, flexible material, said sheet being at least partially wrapped around said core wire.

Preferably said flexible sheet has a wider portion at the proximal and, said wider portion being wrapped at least partially around the core wire, said wider portion having at least one conductive strip extending over said portion in the transverse direction, said at least one strip being electrically connected to a respective lead, said strip(s) forming a contact surface of said male connector, and extending essentially around the entire core wire when said wider proximal portion of said flexible sheet is wrapped around said core wire.

The invention will now be described in detail with reference to the drawings, but the description should not be regarded as limitative on the invention.

BRIEF DESCRIPTION OF THE DRAWINGS

FIG. 1 is a perspective view of a guide wire according to the invention without any outer protective tube;

FIG. 2 shows the guide wire in a state before the flexible circuit board carrying contact elements and leads has been mounted on the core wire;

FIG. 5 is a cross section at 5—5 in FIG. 1;

FIG. 6a shows one embodiment of the contact/lead structure of the invention;

FIG. 6b shows another embodiment of the contact/lead structure of the invention;

FIG. 6c shows a further embodiment of the contact/lead structure of the invention; and FIGS. 7–11 show the sequence of manufacturing steps for the flexible sheet comprising leads and contact elements.

DESCRIPTION OF PREFERRED EMBODIMENTS AND BEST MODE OF OPERATION

Figure 4:
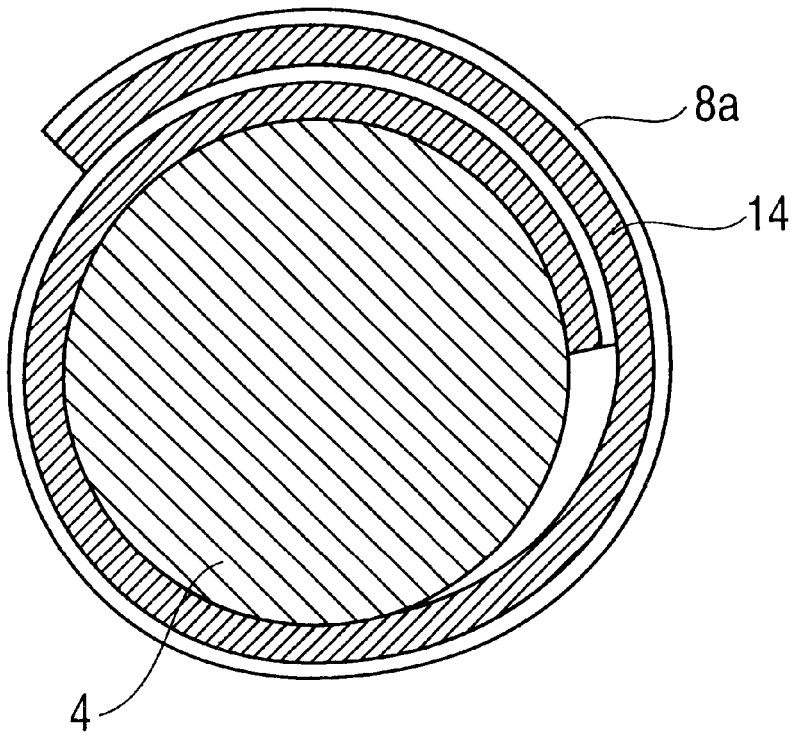
FIG. 4 is a cross section at 4—4 in FIG. 1.

In FIG. 1 there is shown a perspective view of a guide wire 2 comprising a solid core 4 having a distal end where a sensor 6 is mounted in a small recess 12 machined in the core wire. The recess may be simply in the form of flattened portion of the core wire. The guide wire further has a proximal end provided with three contact elements 8a, 8b, 8c (an outer protective tubing is removed for clarity; it is not necessary to provide a protective tubing, but other means of protection are available, e.g. is it possible to apply a layer of lacquer, or a sheet material, or other types of coating). Each contact element is connected to a lead 10a, 10b, 10c respectively, extending along the length of the core wire. The distal end of the leads are connected to the sensor element 6. The core wire is made of e.g. stainless steel, or other materials having similar strength, e.g. carbon fiber. Suitably the diameter of the core wire is approximately 150 $\mu$m.

The contact elements 8a–c and the leads 10a–c are all part of a pattern on a flexible circuit board 14 (more clearly shown in FIG. 2), the pattern having been created by an etch method to be described in detail below. Briefly, the contacts and the leads are made by etching away selected portions from a copper layer on an extremely flexible circuit board sheet (thickness of base film 10–30 $\mu$m, copper layer 10 $\mu$m).

Turning now to FIG. 2, an embodiment of the guide wire is shown in a state before the flexible circuit board 14 comprising contacts 8 and leads 10 is mounted on the core wire 4.

As can be seen in this figure the flexible circuit board has two parts, an elongated part 16, carrying the leads 10a–c, and extending over the entire length of the core wire, and a wider head portion 18, carrying the contact elements 8a–c.

Figure 3:
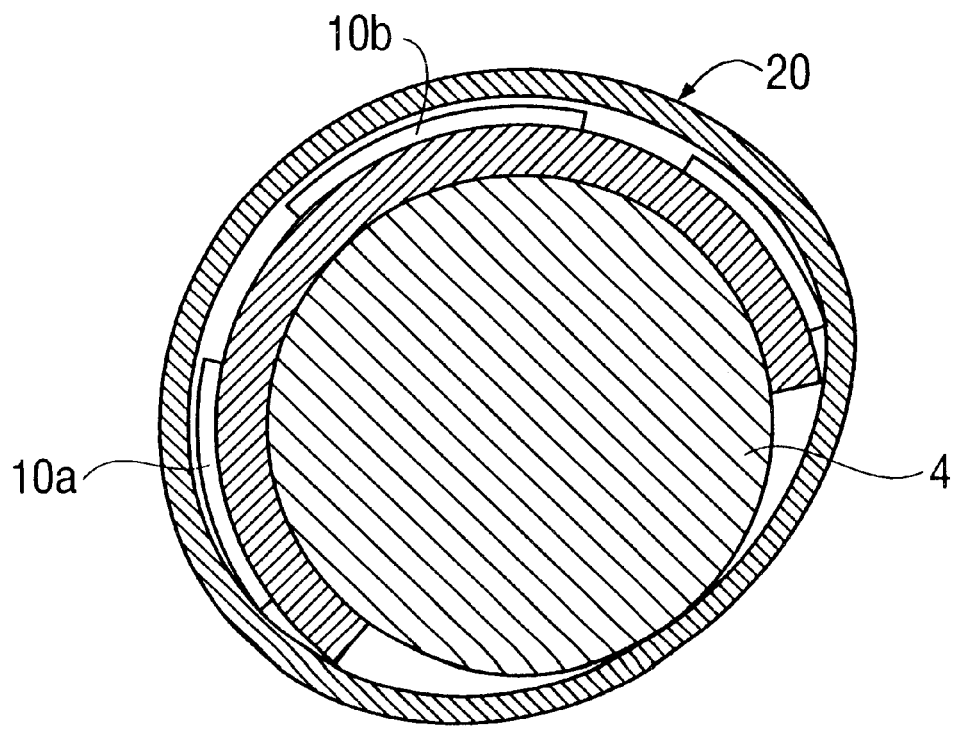
FIG. 3 is a cross section at 3—3 in FIG. 1.

The width of the elongated part 16 is preferably such as to allow the sheet to be wrapped around the core wire. It should cover at least about half the circumference of the core wire. This can be seen in FIG. 3, which is a cross section at 3—3 in FIG. 1. The circumference of the core wire is about 0.3 mm in the at present preferred embodiment. However, at present the sheet is wrapped practically entirely around the core wire. In FIG. 3 also the outer protective tube in the form of a plastic shrink tube 20 is shown. Each lead 10a–c is preferably 60 $\mu$m wide, and the spacing between each lead is about 70 $\mu$m.

In FIG. 4, which is a cross section at 4—4 in FIG. 1 through contact element 8a, the head portion 18 of the flexible circuit board 14 is shown wrapped around the core wire 4 in an overlapping fashion. Preferably the overlap corresponds to about 30% of the circumference of the core wire.

In the preferred embodiment the thin flexible circuit board 14 has the general shape of a "flag pole with a flag" (see FIG.

6a), i.e. an elongated portion 16 extending along the entire length of the core wire, and a rectangular head portion 18 extending laterally from the elongated portion 16. However, it is equally conceivable to shape the thin flexible circuit board in other configurations, such as the one shown in FIG. 6b. The important thing is that each contact element 8 extend essentially across the entire width of the head portion 18.

The width of the head portion 18 should be such as to allow the head portion to be wrapped around the core wire 4 in an overlapping fashion. It must at least overlap to the extent that the lead 10a from the most proximal contact element 8a will be covered by the insulating base film, in order that there be no short circuit when the contact is connected to a mating female connector (such as element 201 in FIG. 1). FIG. 5, which is a cross section taken at 5—5 in FIG. 1, through contact element 8c, and through leads 10a and 10b, illustrates this clearly.

In this preferred embodiment the guide wire is shown having three leads 10a–c and three contact elements 8a–c. Of course it is conceivable and within the inventive concept to have any number of leads and contacts, from one single lead, and up to a number which is only limited by the obtainable manufacturing accuracy. The spacing between leads would in this regard set an upper limit on the number of leads.

Although the embodiment described above is the at present preferred embodiment, other alternative designs are conceivable and within the inventive concept.

Thus, it is possible to have each lead 10a–c simply terminate in a slightly widened portion 8'a–c, forming a point of contact (see FIG. 6c), which does not extend entirely around the core wire. In such a case the corresponding female contact elements will have be to be designed so as to insure adequate contact regardless of how the male connector is oriented. Furthermore, in order not to cause short circuiting across the leads by the female contact elements, it would be necessary to cover each individual lead up to its respective point of connection to the respective point of contact 8'a–c, with a thin layer 22 of some insulating material. This could be a thin lacquer layer, or a polymer layer having good insulating properties. The thickness of this layer will have to such as to not extend above the surface of the points of contact. The insulating layer should extend over an area corresponding at least to the area within which the female connector makes electrical contact with the contact members of the male connector.

Also, it is not essential that the lead(s) extend all the way to the distal end. It is possible to let the flexible sheet carrying its leads terminate somewhere along the core wire, and have standard leads connecting thereto, and to the sensor.

Figure 7:
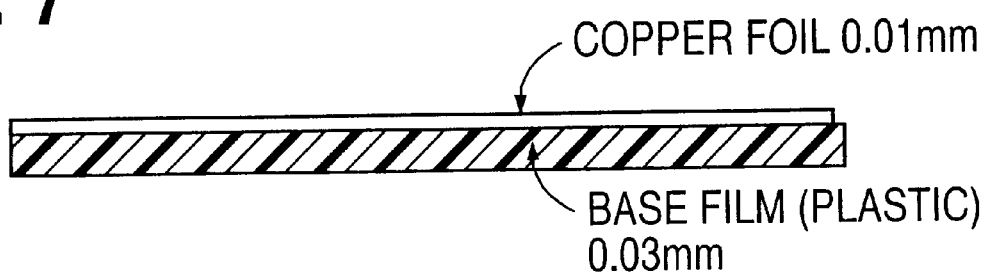
Figure 8:
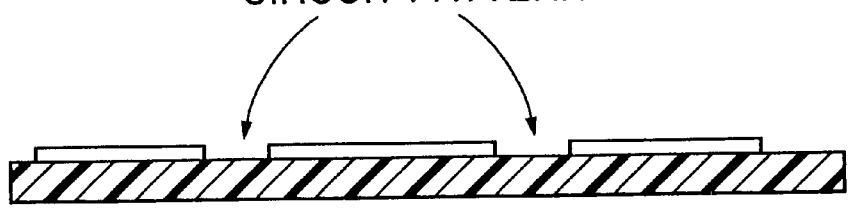

With reference to FIGS. 7–8, the etch method for manufacture of the flexible circuit board comprising the lead and contact pattern will be described.

The starting material is a sheet of a thin, flexible plastic film (see FIG. 7) e.g. polyimide film, on the surface of which a layer of copper has been deposited. Such material are commercially available under the trademark KAPTONE®, obtainable from Du Pont.

The thickness of the plastic sheet is about 12 μm, and the copper layer is about 9 μm.

The desired lead and contact pattern is applied to the copper foil by conventional means, by covering the areas with a protective agent, so as to protect the copper from the aggressive etch liquids. The sheet is exposed to a suitable etch whereby the material not protected by the protective agent is removed (see FIG. 8), leaving a lead/contact structure (see FIGS. 6a–c). Of course a large sheet may be provided with a multiplicity of patterns, and after etching individual structures are cut out or machined in other ways.

There are various options for the connection between the flexible circuit board carrying the leads, and the sensor chip.

Embodiments thereof will now be described with reference to FIGS. 9–11.

In FIG. 9 a method of connecting the chip to the circuit board carrying the leads is shown, using ordinary cables 24 having circular cross section, however with extremely small diameter, for interconnecting the chip and the circuit board. The leads are soldered or bonded to contact pads 26 on the chip 6 at one end and to the circuit board at the other.

FIG. 10 illustrates a method where the circuit board is connected by soldering directly onto contact pads 26 on the chip 6. Thereby solder may be applied to one of the surfaces, and a method known as the "flip-chip method" may be employed for attachment. This method requires a copper layer on both (opposing) sides of the board, and also that the circuit board has been plated through, i.e. by making a hole 28 in the board and plating the hole to create the required electrical contact between the layers.

In FIG. 11 a third embodiment is disclosed. It comprises providing an intermediate circuit board 30 having a contact 32 /lead 34 pattern matching both the terminal ends of the leads on the lead circuit board and the contact pads 26 on the chip. The intermediate board is a single layer circuit board having an opposite orientation in terms of its conductive layer in relation to the main circuit board, i.e. it faces downwards.

The connection of this intermediate board 30 is made in essentially the same way as for the embodiment of FIG. 10.

The insulating film provides the male contact with a smooth outer surface. The smooth outer surface may be easily cleaned from blood for connecting to the female contact. The insulating material is continuous, thereby preventing capillary action by bodily fluids which would otherwise allow a short circuit. Also, the male connector presents a relatively smooth surface that can be easily cleaned of blood or body fluids with a wiping device, for example, a rubber ring or o-ring mounted in a female contact.

What is claimed is:

1. A guide wire, comprising:
   a) a core wire having a proximal and a distal end;
   b) at least one electrical lead provided on said core wire and extending along the length thereof, and adapted for connection to an electrical device provided at the distal end of said core wire;
   c) a male connector means provided at the proximal end of said core wire;
   d) a protective layer covering the core wire and said at least one electrical lead;
   e) wherein said at least one electrical lead, at least partially along the length of said core wire, is formed on a sheet of thin, flexible material;
   f) said at least one lead terminating at said male connector means at the proximal end in a contact element adapted for a mating female connector.

2. The guide wire as claimed in claim 1, further comprising at least two electrical leads, said leads being covered by an insulating material such as to not be short circuited by female contact elements in a mating female connector, said female contact elements corresponding respectively to one male contact point.

3. A guide wire, comprising:

a) a core wire having a proximal and a distal end;

b) at least one electrical lead provided on said core wire and extending along the length thereof, and adapted for connection to an electrical device provided at the distal end of said core wire;

c) a male connector means provided at the proximal end of said core wire;

d) a protective layer covering the core wire and said at least one electrical lead;

e) wherein said at least one electrical lead, at least partially along the length of said core wire, is formed on a sheet of thin, flexible material;

f) said at least one lead terminating at said male connector means at the proximal end in a contact element adapted for a mating female connector, wherein said at least one lead and said contact element are formed by etched conductive material provided on said sheet.

4. The guide wire as claimed in claim 3, wherein said thin, flexible material includes polyimide, and said conductive material includes copper.

5. A guide wire:

a) a core wire having a proximal and a distal end;

b) at least one electrical lead provided on said core wire and extending along the length thereof, and adapted for connection to an electrical device provided at the distal end of said core wire;

c) a male connector means provided at the proximal end of said core wire;

d) a protective layer covering the core wire and said at least one electrical lead;

e) wherein said at least one electrical lead, at least partially along the length of said core wire, is formed on a sheet of thin, flexible material;

f) said at least one lead terminating at said male connector means at the proximal end in a contact element adapted for a mating female connector, wherein said sheet has a wider portion at the proximal end, said wider portion being wrapped at least partially around the proximal end of said core wire.

6. The guide wire as claimed in claim 5, where said wider portion has at least one conductive strip extending over said portion in the transverse direction, said at least one strip being electrically connected to a respective lead.

7. The guide wire as claimed in claim 6, wherein each of said strips forms a contact surface of said male connector, and extends at least partially around the core wire when said wider proximal portion of said sheet is wrapped around said core wire.

8. The guide wire as claimed in claim 5, wherein said wider portion extends around said core wire and overlaps itself.

9. The guide wire as claimed in claim 1, wherein said sheet is at least partially wrapped around said core wire.

10. A guide wire, comprising:

a) a core wire having a proximal and a distal end;

b) at least one electrical lead provided on said core wire and extending along the length thereof, and adapted for connection to an electrical device provided at the distal end of said core wire;

c) a male connector means provided at the proximal end of said core wire;

d) a protective layer covering the core wire and said at least one electrical lead;

said at least one electrical lead being formed on a sheet of thin, flexible material;

e) said sheet being at least partially wrapped around said core wire along the length thereof;

f) said sheet having a wider portion at the proximal end;

said wider portion being wrapped at least one full turn around the proximal end of said core wire;

g) said wider portion having at least one conductive strip extending over said portion in the transverse direction;

h) said at least one strip being electrically connected to a respective lead;

i) each strip forming a contact surface of said male connector means, and extending essentially around the entire core wire when said wider proximal portion of said flexible sheet is wrapped around said core wire.

11. The guide wire as claimed in claim 1, further comprising three electrical leads and three contact surfaces.

12. The guide wire of claim 11, further comprising a plurality of contact pads on said electrical device corresponding to said leads, for attaching terminal ends of said leads to said contact pads thereby forming a connection between leads and said electrical device.

13. A guide wire, comprising:

a) a core wire having a proximal and a distal end;

b) at least one electrical lead provided on said core wire and extending along the length thereof, and adapted for connection to an electrical device provided at the distal end of said core wire;

c) a male connector means provided at the proximal end of said core wire;

d) a protective layer covering the core wire and said at least one electrical lead;

e) wherein said at least one electrical lead, at least partially along the length of said core wire, is formed on a sheet of thin, flexible material;

f) said at least one lead terminating at said male connector means at the proximal end in a contact element adapted for a mating female connector;

said guide wire further comprising:

g) three electrical leads and three contact surfaces;

h) a plurality of contact pads on said electrical device corresponding to said leads, for attaching terminal ends of said leads to said contact pads thereby forming a connection between leads and said electrical device; and i) an intermediate circuit board having a first end with a lead pattern matching said leads and contact pads attached to the terminal ends of said leads, and a second end attached to said contact pads.

14. The guide wire of claim 13, further comprising a connection between said leads on said flexible circuit board and said electrical device formed by first ends of intermediate insulated electrical wires attached to respective leads, and second ends of said wire attached to contact pads.

15. The guide wire of claim 1, wherein said electrical device is a pressure sensor.

16. The guide wire of claim 10, wherein said electrical device is a pressure sensor.

17. A method of precluding contamination by human or animal body fluids and the like in an electrical connection having a male member and a female member, comprising:

a) providing an elongated guide wire having a proximal end and a distal end, the male member being positioned at the proximal end;

b) forming a generally smooth surface on the male member, the member comprising a plurality of electrical conductors thereon and including forming a conductive layer on a sheet of thin, flexible material and etching away conductive material to form the plurality of conductors;

c) inserting the distal end of the guide wire into the body in the presence of the body fluids;

d) sliding a catheter over the guide wire and into the body wherein body fluids surround and enter at least a portion of the catheter;

e) engaging the male member into the female member, the female member having complementing conductors therein;

f) disengaging the male and female members;

g) removing the catheter from the body by sliding the catheter over the guide wire wherein body fluids are deposited on the smooth surface of the male member; and h) removing the body fluids from the smooth surface without leaving body fluid on or between the conductors, thus precluding contamination.

* * * * *